United States Patent [19]

Orenstein et al.

[11] Patent Number: 5,120,221
[45] Date of Patent: Jun. 9, 1992

[54] DENTAL CLAMP FOR USE IN IMPLANT RESTORATIVE DENTISTRY

[76] Inventors: Jonathan H. Orenstein, 116 Kings Croft, Cherry Hill, N.J. 08034; Stephen R. Cohen, 1024 Bob White, Cherry Hill, N.J. 08003

[21] Appl. No.: 458,958

[22] Filed: Dec. 29, 1989

[51] Int. Cl.⁵ .............................................. A61C 3/14
[52] U.S. Cl. ................................................ 433/159
[58] Field of Search .............. 433/159, 160, 4, 173, 433/174

[56] References Cited

U.S. PATENT DOCUMENTS

| | | | |
|---|---|---|---|
| 390,561 | 10/1888 | Brown | |
| 732,288 | 6/1903 | Felsch | 433/159 |
| 816,828 | 4/1906 | Smith | |
| 1,636,861 | 7/1927 | Griveau | |
| 1,688,670 | 10/1928 | Swendiman | |
| 1,722,893 | 7/1929 | Burnier | |
| 2,253,132 | 8/1941 | Malson | 32/63 |
| 2,602,227 | 7/1952 | Kempe | 32/63 |
| 2,632,248 | 3/1953 | Kohler | 32/62 |
| 2,725,632 | 12/1955 | Rabben | 32/66 |
| 2,754,591 | 7/1956 | Schweizer | 32/68 |
| 3,507,043 | 4/1970 | Rubin | 32/63 |
| 3,713,222 | 1/1973 | Tofflemire | 433/159 |
| 3,834,026 | 9/1974 | Klein | 433/159 |
| 4,001,940 | 1/1977 | Cusato | 32/40 R |
| 4,035,917 | 7/1977 | Roberts | 32/40 R |
| 4,040,186 | 8/1977 | Kalvelage | 32/66 |
| 4,081,909 | 4/1978 | Garcia | 32/66 |
| 4,197,647 | 4/1980 | Goldenthal | 433/159 |
| 4,310,305 | 1/1982 | Frajdenrajch | 433/4 |
| 4,330,891 | 5/1982 | Branemark | 3/1 |

OTHER PUBLICATIONS

Book entitled "Instrumentation for the Operating Room" by S. M. Brooks, published in 1983 by C. V. Mosby Company, St. Louis, MO, pp. 1, 2, 4, 11-16, 50, 81, 91, 133, 136, 179, 186, 239, 242, 247, 248, 250, 266, 269, 276, 281, 290, 292, 293, 298, 339, 372, 378, 400, 416.

Brochure entitled "The Unique Method of Tissue Integration That Offers Patients New Quality of Life" published in 1985 by Nobelpharma, Goteborg, Sweden (24 pages including covers).

Product Catalog of Nobelpharma, Goteborg, Sweden re Nobelpharma Implant System, 1987.

*Primary Examiner*—Robert P. Swiatek
*Assistant Examiner*—Nicholas D. Lucchesi
*Attorney, Agent, or Firm*—Volpe and Koenig

[57] ABSTRACT

This dental clamp is for gripping a cylindrical abutment that is (i) mounted on an endosseus-type fixture that is implanted into a host jawbone and (ii) is located with its superior end tending to be flush with or beneath the exposed surface of gum tissue closely surrounding the abutment. The clamp comprises a pair of arms crossing each other in scissors fashion and a pivot joining the arms so that the portions of the arms on one side of the pivot constitute handles and the portions on the other side of the pivot constitute working portions. The working portions have free ends and confronting faces near the free ends that are movable together in response to the handles being moved together. Projecting laterally from the working portions are two flanges that bound a space of generally cylindrical form when the confronting faces are close together. Each of these flanges is shaped so as to be insertable between the abutment and the surrounding gum tissue. The flanges are adapted to grip the abutment therebetween in response to the handles being urged together when the flanges have been inserted between the abutment and the surrounding gum tissue.

10 Claims, 6 Drawing Sheets

DENTAL CLAMP FOR USE IN IMPLANT RESTORATIVE DENTISTRY

BACKGROUND

This invention relates to a dental clamp for use in implant restorative dentistry and, more particularly, relates to a dental clamp of this type which can be used for establishing a firm and stable grip upon implant hardware that has its superior end positioned flush with or just beneath the surface of gum tissue closely surrounding the hardware.

In certain implant restorative dentistry, an endosseus fixture in the form of a titanium pin is anchored in the jawbone of the patient by inserting this pin into a closely-fitting hole provided in the jawbone of the patient and relying upon tissue integration to develop a bond between the titanium oxide coating on the pin and the closely-surrounding host bones. In one application of this type, the pins and the hole are provided with mating threads to provide, among other things, a greater bonding area for tissue integration between the pin and the surrounding bone. In another application, an unthreaded pin is inserted into a closely surrounding unthreaded hole provided in the jawbone, and a good bond is developed between the pin and the surrounding host bone by tissue integration without assistance from mating threads.

After the above-noted tissue integration has sufficiently developed, a dental prosthesis is mounted on the fixture, being attached thereto by means comprising a screw that is threaded into an internally threaded hole in the fixture or connected structure. For properly positioning the prosthesis on the fixture, a tubular abutment of preselected length is mounted on the fixture between the fixture and the prosthesis by means that prevents the abutment from rotating with respect to the fixture. In the newer applications of this technique, the superior end of the abutment, instead of being exposed, is positioned flush with or just beneath the surface of the surrounding gingiva.

When a prosthesis is to be attached to the fixture, it is customary to clamp the abutment so that it is fixed against rotation while the above-referred-to attaching screw is being threaded into the fixture. This clamping action protects the biologic integrity of the bond between the implanted fixture and the host bone by preventing this bond from being overstressed and possibly damaged by torsional forces applied to the attaching screw.

If the abutment is located with its superior end flush with or beneath the surface of the surrounding gingiva, it is difficult to firmly clamp the abutment so as to hold it against rotation. There is no apparent readily accessible portion of the abutment that can be grasped to hold the abutment and the fixture coupled thereto against rotation.

OBJECTS

An object of our invention is to provide, for use in implant restorative dentistry, a dental clamp that can be used to grasp an abutment of the above type that is located with its superior end flush with or just beneath the exposed surface of the surrounding gingiva.

Another object is to provide a dental clamp of this type that can be used to establish a firm and stable grip on the abutment without marring the surface of the abutment.

Still another object is to provide a dental clamp capable of carrying out the immediately preceding objects with reduced interference from nearby naturally-occurring hard and soft tissue and from any other prosthetic devices in the patient's mouth.

SUMMARY

In carrying out the invention in one form, we provide a dental clamp for use in gripping an abutment of the above-described type that is located with its superior end substantially flush with or beneath the exposed surface of gum tissue closely surrounding the abutment. The clamp comprises a pair of arms crossing each other in scissors fashion and a pivot pivotally joining the arms so that the portions of the arms on one side of the pivot constitute handles and the portions on the other side constitute working portions. The working portions have free ends and confronting faces near the free ends that are movable together in response to the handles being moved together. Aligned recesses in the confronting faces together define an opening that extends through said working portions when the confronting faces are in close proximity. On these working portions, we provide flanges projecting therefrom in a location such that the space between the flanges is substantially aligned with said opening when the confronting faces are in close proximity. Each of the flanges is shaped so as to be insertable between said abutment and the gum tissue that closely surrounds the abutment.

In one embodiment, each of the flanges has a generally semi-cylindrical inner surface bordering the inter-flange space and an outer surface generally in the shape of a section of a truncated cone having a base adjacent said working portions.

BRIEF DESCRIPTION OF FIGURES

For a better understanding of the invention, reference may be had to the following description taken in conjunction with the accompanying drawings, wherein.

DETAILED DESCRIPTION OF EMBODIMENT

Figure 1:
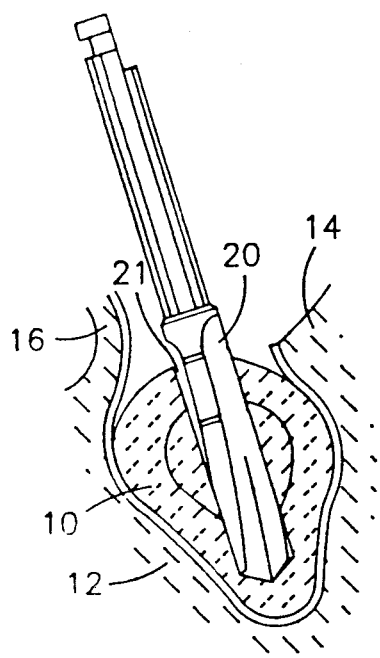
FIG. 1 is a cross-sectional view through a jawbone showing a hole being drilled in the jawbone as part of an implant operation.
Figure 2:
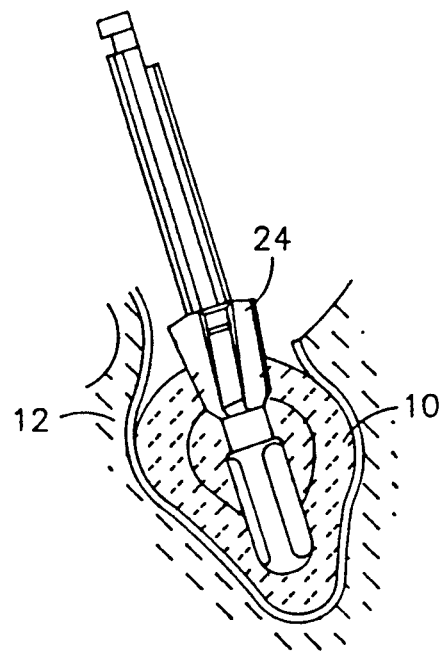
FIG. 2 is a cross-sectional view taken in the same location as FIG. 1 showing a countersinking operation at the entrance to the hole of FIG. 1.

The early stages of an implant operation are illustrated in FIGS. 1 and 2. These stages occur under a local or general anesthesia.

Referring first to FIG. 1, the patient's jawbone 10 is shown in transverse cross section, and the soft tissue surrounding the jawbone is shown at 12. An appropriate incision has been made in the gingiva or gum, 14 and the portion of the gingiva 16 normally located above the jawbone site where the implant is to be installed has been displaced to expose this portion of the jawbone. The displaced gum portion is referred to hereinafter as a mucous flap. The jawbone illustrated in FIG. 1 has been drilled with successively wider spiral drill bits, the last one of which 20 is shown still in place in FIG. 1. When the drill bit 20 has been removed from the drilled hole 21, the entrance to the hole is countersunk as shown in FIG. 2. The countersink bit is shown at 24 in FIG. 2.

Figure 3:
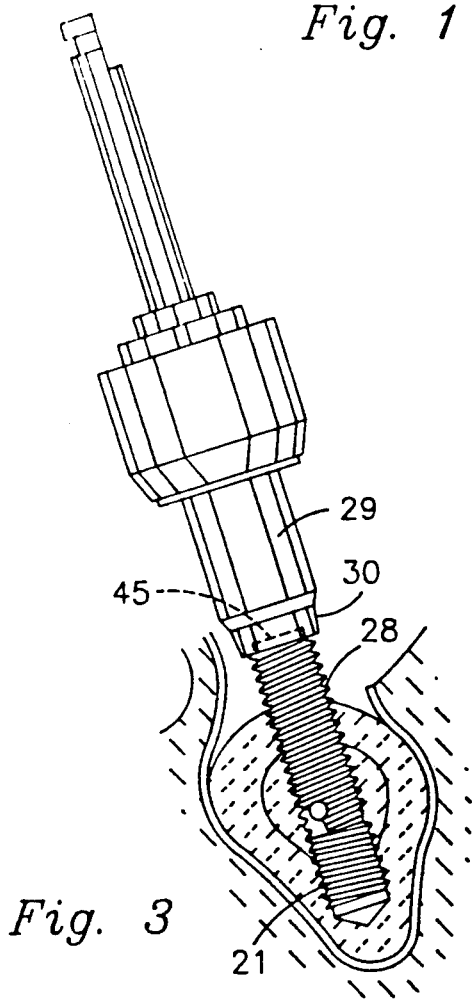
FIG. 3 shows an externally threaded metal fixture being installed in the hole of FIGS. 1 and 2 after the hole has been tapped to provide internal threads therein.

Next, the drilled hole 21 in the jawbone 10 is internally threaded by means of an appropriate tap burr (not shown) inserted into the hole and suitably rotated. Then, as shown in FIG. 3, a threaded titanium anchorage unit, or fixture, 28 in the form of an externally-threaded pin is threaded into the tapped hole 21, using a conventional wrench 29. The fixture 28 has a slightly enlarged head 30 that fits into the countersink when the fixture is fully threaded into the hole 21. Threading forces are transmitted from the wrench 29 to the fixture through a hexagonal projection 45 in the head 30 that mates with a correspondingly shaped socket in this wrench.

Figure 4:
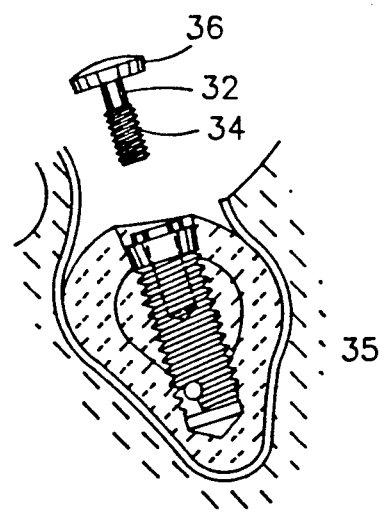
FIG. 4 is an exploded view showing a cover screw in readiness for being threaded into the fixture of FIG. 3 after the fixture has been installed.

After the fixture 28 has been threaded in the jawbone as above described, the mucous flap 16 over the fixture is restored to its initial position and is sutured in place to begin a healing process. But before the mucous flap 16 is so restored, a cover screw 32, shown in FIG. 4, is installed in the fixture. This cover screw 32 has an externally threaded portion 34 that is threaded into an internally threaded hole 35 on the central longitudinal axis of the fixture 28. The head 36 of the cover screw fits over the top of the fixture and serves to prevent bone growth over this fixture head during the healing process. During the healing process, the bond is developed through tissue integration between the titanium oxide layer on the outer surface of the titanium fixture 28 and the surrounding host bone.

When the healing process has been sufficiently completed, the next surgical stage begins. With a circular punch (not shown), the surgeon excises the mucosa above the fixture head 30 and then removes the cover screw 32. He then cleanses all hard and soft tissue remnants from the fixture head.

Figure 5:
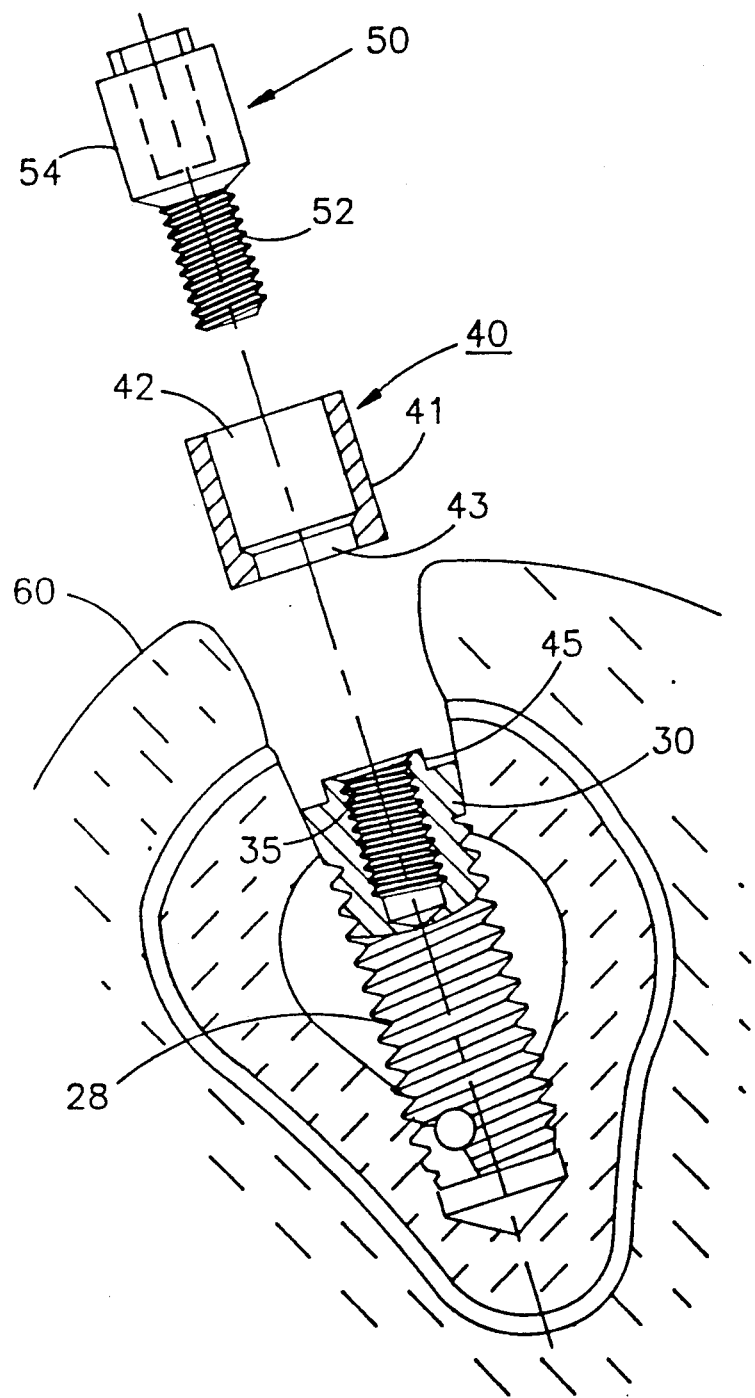
FIG. 5 is an enlarged exploded view taken in the same location as FIG. 1–4 but showing a tubular abutment and attaching screw that are installed at a later stage of the implant operation.

Next he mounts on the fixture head a tubular abutment of preselected length that serves to properly locate the prosthesis (soon to be described) on the fixture head. This tubular abutment is best shown in FIG. 5 at 40. Abutment 40 has a smooth cylindrical outer surface 41 and a bore 42 that is of reduced size and hexagonal shape at its lower end, as shown at 43. The hexagonal portion 43 of the bore is adapted to receive the hexagonal projection 45 integral with the top of the fixture head 30. When the abutment 40 engages the fixture head, hexagonal portions 45 and 43 fit closely together and serve to block the tubular abutment 40 from rotating with respect to the fixture 28.

Figure 8:
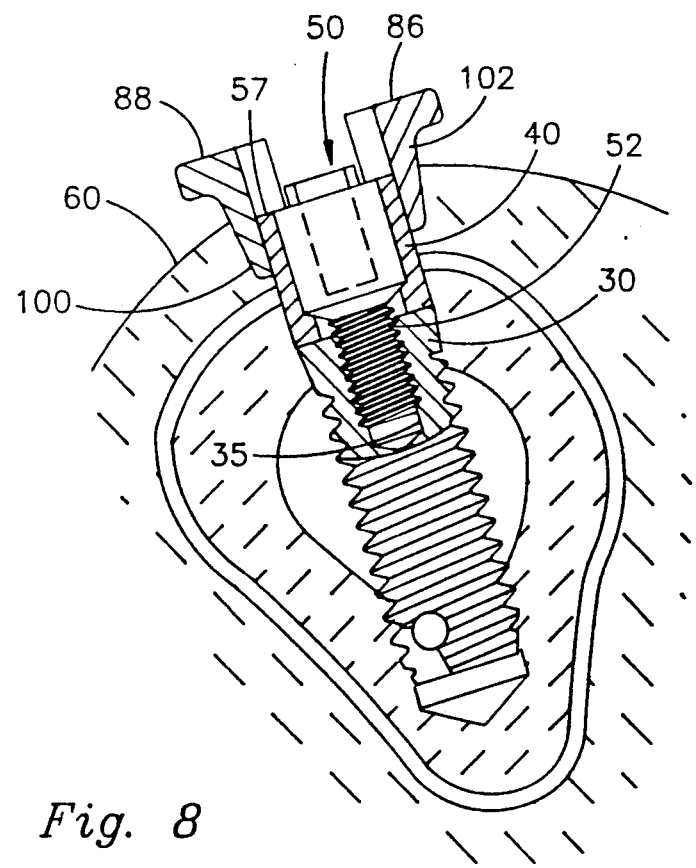
FIG. 8 is a view similar to that of FIG. 6 except showing the abutment being gripped by a portion of the clamp of FIG. 7.

The tubular abutment 40 is held in place on the fixture head by a screw 50 that has an externally-threaded portion 52 that extends through the bore of the abutment (FIG. 8). This threaded portion 52 is received in the threaded hole 35 in the fixture 28. When the abutment 40 is in place, the screw 50 is threaded into the hole 35 and clamps the abutment between the head 54 of the screw and the head 30 of the fixture 28. When abutment 40 is thus clamped, the hexagonally shaped portions 45 and 43 mate and fit closely together, thus blocking rotation of the abutment with respect to the fixture.

Figure 6:
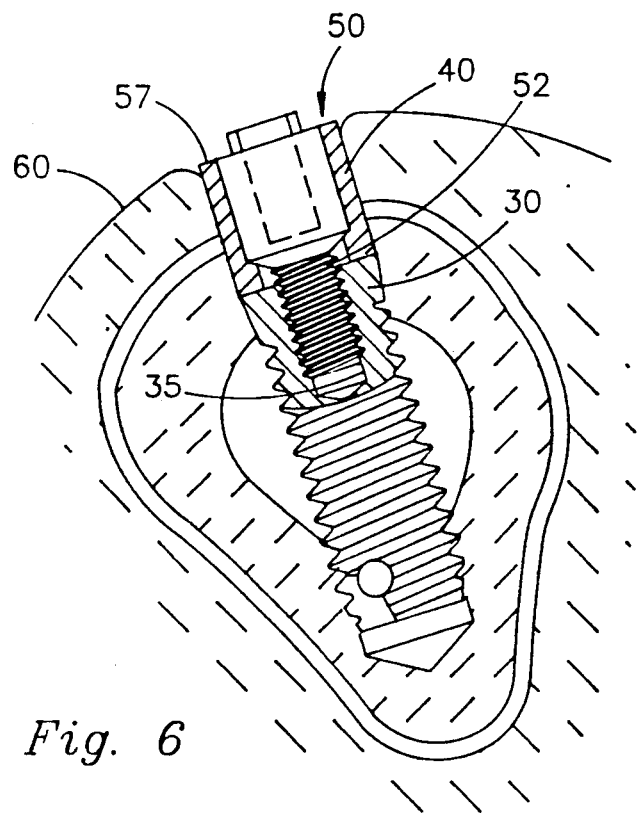
FIG. 6 is a view similar to that of FIG. 5 except showing the components of FIG. 5 installed.

After the abutment 40 has been installed in this manner, the surrounding gingiva is allowed to heal. As shown in FIG. 6, this results in the gingiva tightly surrounding the abutment and the superior surface 57 of the abutment being substantially flush with the exposed surface 60 of the gingiva. Usually, the gingiva as it heals will develop a cuff of healthy tissue closely surrounding the outer surface of the abutment 40.

In referring in the preceding paragraph and elsewhere in this application to the "superior" surface of the abutment, we are referring to the surface of the abutment that is located furthest from the jawbone when the abutment is installed. This will be the top surface of an abutment mounted on the lower jawbone and the bottom surface of an abutment mounted on the upper jawbone. Similarly, in referring to "beneath" the exposed surface of the gum, we intend to denote: being on the side of the gum surface nearest the supporting jawbone.

Figure 9:
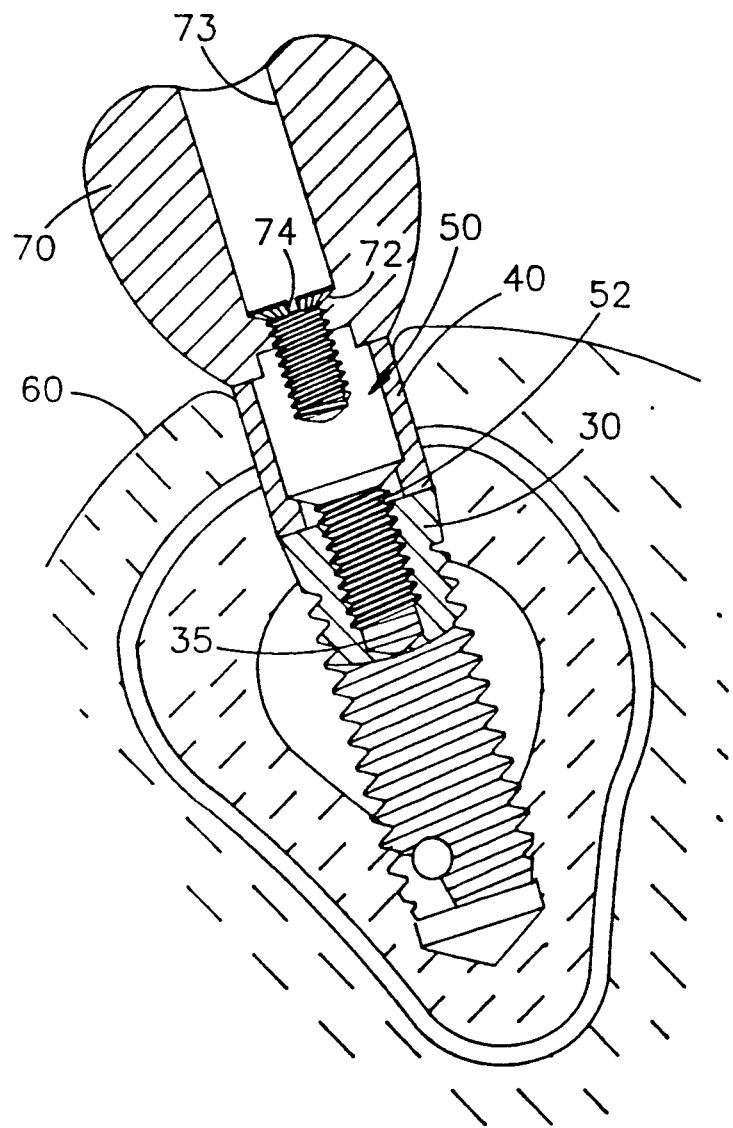
FIG. 9 is a view similar to that of FIG. 6 except showing a prosthesis in the form of a single tooth mounted atop the abutment and fixture of FIG. 6.

After a prosthesis has been made and fitted in a known manner, it is attached to the fixture 28 in a portion atop the abutment 40. FIG. 9 shows such a prosthesis, in the form of a single tooth, at 70, the prosthesis being held in its illustrated position by another screw 72 extending through a hole 73 in the prosthesis and into a threaded hole 74 in the head of the attaching screw 50. The screw 72 is tightened by a suitable screw driver (not shown) having a blade that is adapted to extend through the hole 73 and into a kerf 74 in the head of the screw 50.

To protect the integrity of the bond between the endosseous fixture 28 and the surrounding jawbone against damage from forces produced by tightening of either of the screws 50 or 72, it is highly desirable to clamp the abutment 40 against rotation during the screw-tightening operations. Since the abutment 40 is, in effect, splined to the fixture 28, this clamping of the abutment will block the fixture from turning in the threaded hole in the jawbone and thus will protect the biologic integrity of the bond between the endosseous implant and the surrounding host bone.

Figure 7:
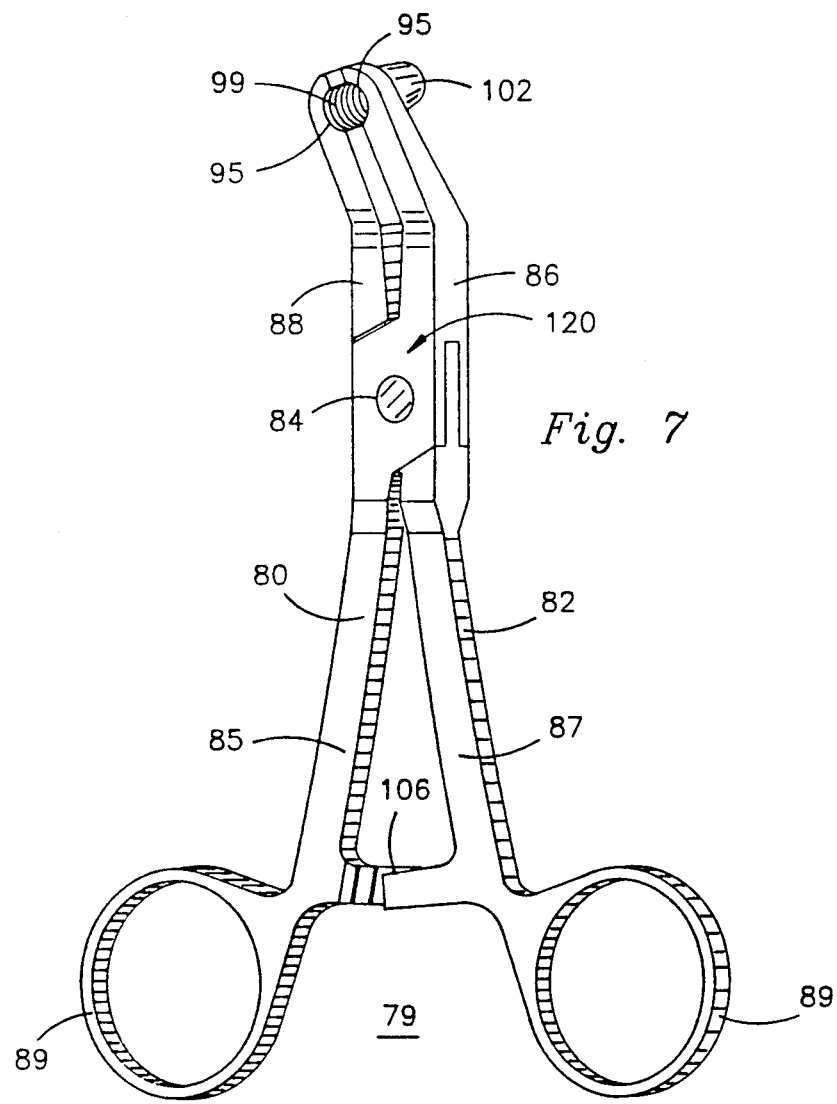
FIG. 7 is a perspective view of a dental clamp embodying one form of our invention and used in the implant operation.

For clamping the abutment 40 during this period so as to prevent its rotation, we provide the special pliers-type clamp 79 shown in FIG. 7. This clamp comprise two arms 80 and 82 crossing each other in scissors relation and coupled together by a pivot pin 84 extending between the two arms. Arm 80 comprises a handle portion 85 on one side of pivot 84 and working portion or jaw, 86 on the other side of the pivot. In a similar manner, the other arm 82 comprises a handle portion 87 on one side of the pivot 84 and a working portion, or jaw 88, on the other side of the pivot. Each handle has a finger grip 89 at its extreme end.

Adjacent the free end 90 of each of the jaws 86 and 88 there is a face confronting the other jaw, and in each of these faces 92 and 94 there is a recess 95 of generally and approximately semi-cylindrical configuration. When the faces 92 and 94 are in juxtaposition, the recesses 95 are in alignment and define a generally cylindrical opening 99 of generally circular cross section extending from one side to the other of the jaws proper.

Projecting laterally from the jaws at one side of the jaws are two flanges 100 and 102 one facing the other and each having an inner surface of generally semi-cylindrical form. When the faces 92 & 94 are in juxtaposition, these flanges define between them an opening 103 of generally cylindrical form which is aligned with and of the same size as the opening 99 in the jaws proper. When the faces 92 and 94 are in juxtaposition, the external surfaces 105 and 106 and the flanges together define a truncated cone that is rounded off at its free end.

The above-described shape of the flanges 100 and 102 enable the surgeon using the clamp 79, after he has aligned the openings 99 and 103 with the abutment 40, readily to insert the flanges between the abutment and the surrounding tight cuff of gum tissue. Such insertion is facilitated by the relative thinness of the flanges at their free ends, by the rounded configuration of the flanges at their free ends, and by the overall shape of the flanges, especially, the features that they can closely surround the cylindrical abutment and they consume very little space considered radially of the abutment, particularly at their free ends.

When the flanges 100 and 102 have been inserted between the abutment 40 and the surrounding gum tissue, the surgeon, with his fingers in the grips 89, squeezes the handles 85 and 87 together, thus urging the jaws 86 and 88 together, thereby exerting a firm and stable grip on the abutment. This allows him to thread into place and together each of the screws 50 and 72 without developing on the mixture 28 rotational forces that could rotate the fixture in its threads and thus damage the biologic integrity of the bond between the fixture and the surrounding host bone.

In a preferred form of our invention, the pliers-type clamp 79 includes reclosable locking means 106 of conventional form (e.g. serrated) locking the handles 85 and 87 in relative portions where the jaws 86 and 88 firmly grip the abutment 40. Locking the handles 85 and 87 in this manner allows the surgeon to discontinue squeezing the handles together without detracting from his firm grip on the abutment. Typically, even though not squeezing the handles together during this period, he will nevertheless maintain his fingers within the grips 89 to prevent rotation of this abutment 40 while tightening the screws 50 and 72.

Figure 10:
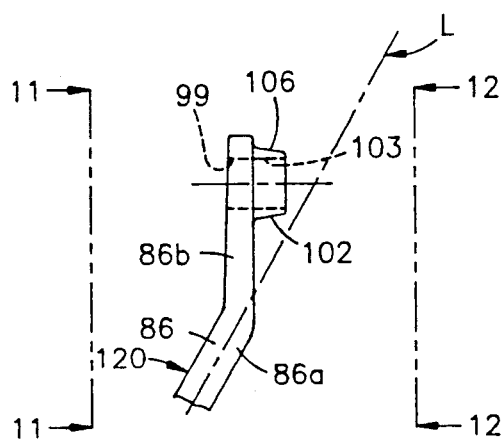
FIG. 10 is a side elevational view of the working portions, or jaws, of the clamp of FIG. 7.

A significant feature of our clamp is that the jaws 86 and 88 are bent, as best shown in FIGS. 7 and 10. Each jaw may be thought of as having a proximate portion near pivot 84 and a distal portion near its free end. In FIG. 10, the proximate portion of jaw 86 is designated 86a and the distal portion 86b. The plane of the proximate portion 86a of the jaw 86 is illustrated at 120 in FIG. 10. The plane of the distal portion 86b is disposed at an angle of about 30 degrees with respect to the plane 120. The handle 85 that is coupled to jaw 86 is located in substantially the same plane 120 as the proximate portion of the jaw. The other handle 87 and the proximate portion of its associated jaw 88 are also located in the plane 120. The distal portions of the two jaws are substantially coplanar. Plane 120 may be thought of as a reference plane that is normal to the axis of pivot 84. Longitudinal handle axis L extends with plane 120 in proximate jaw portion 86A.

Figure 11:
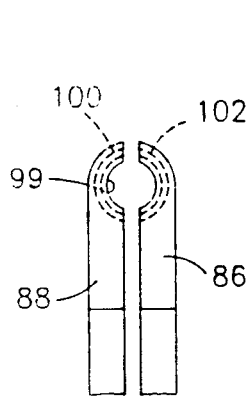
FIG. 11 is a plan view of the jaws of FIG. 10 taken in the direction of line 11—11 of FIG. 10.
Figure 12:
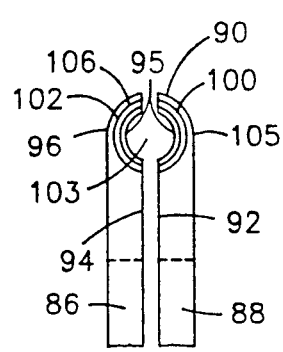
FIG. 12 is a plan view of the jaws of FIG. 10 taken in the direction of the line 12—12 of FIG. 10.

In an intraoral setting, the bent configuration of the jaws 86 and 88 are usually accessable to the abutments (such as 40). Typically, in this intraoral setting there are obstructions in the form of naturally-occurring had and soft tissue or possibly other prosthetic devices, and the bend in the jaws allows the surgeon to more easily avoid these obstructions while using the clamp. It is to be understood that angles different from the specific angle illustrated will oftentimes afford easier access to particular abutments, depending upon their location and the location of the intraoral obstructions. We, therefore, plan to make available a set of clamps, each substantially the same as illustrated in FIGS. 7 and 11-12, but with different angles at preselected values between 0 and 90 degrees to accomodate these different working conditions.

It is to be noted that the flanges 100 and 102 extend from the distal portions of the jaws approximately at right angles to these distal portions (FIG. 10). This right angle relationship facilitates insertion of the flanges into their desired positions between the abutment and the surrounding cuff of gum tissue.

In the illustrated embodiment of the invention, the inner surfaces of the flanges 100 and 102 that define the opening 10e are smooth. This enables them to tightly grip the abutment 40 without scratching or otherwise marring the external surfaces of the abutment.

It is also to be noted that the opening 99 in the jaws 88 and 86 proper allows an attaching device (such as screw 50, FIG. 8) to extend freely through the jaws, even when the jaws are close together and the flanges 100 and 102 are gripping abutment 40.

While we have described above how our clamp are used to assist in tightening the attaching screws 50 and 72 during installation of the illustrated abutment and prosthesis, it is to be understood that the clamp is also usable to assist in loosening the attaching screws during removal or adjustment of this hardware. By clamping the abutment 40 while the screws 50 and 72 are being loosened during such removal or adjustment, we are able to avoid undesired rotation of the fixture 28 in the surrounding hole in the jawbone structure thus preventing damage to the biologic integrity of the bond between the fixture and surrounding host bone.

While we have described our clamp as being used for implantation of hardware in the lower jaw, or mandible, it is to be understood that the clamp is equally useful for implantation of hardware in the upper jaw, or maxilla. The bend in the working portion of the clamp serves equally well during such upper jaw implantation to avoid intraoral obstructions and to improve accessibility of the abutments such as 40 to their being grasped by the surgeon.

While the illustrated implant includes mating threads between the fixture 28 and the surrounding host bone, it is to be understood that the invention is equally useful in connection with the type of implant that has no threads in this region. In this latter type of implant, an unthreaded titanium pin is inserted into a closely surrounding hole in the jawbone, and a good bond is developed between the pin and the host bone through tissue integration without reliance upon any threads in this region. An abutment such as the illustrated abutment 40 and a prosthesis corresponding to that shown are attached to such a fixture in the same manner as illustrated. Clamping the abutment to preclude its rotation during tightening and loosening of the attaching screws serves to protect the biologic integrity of the bond in the same manner as above described.

Figures 13, 14:
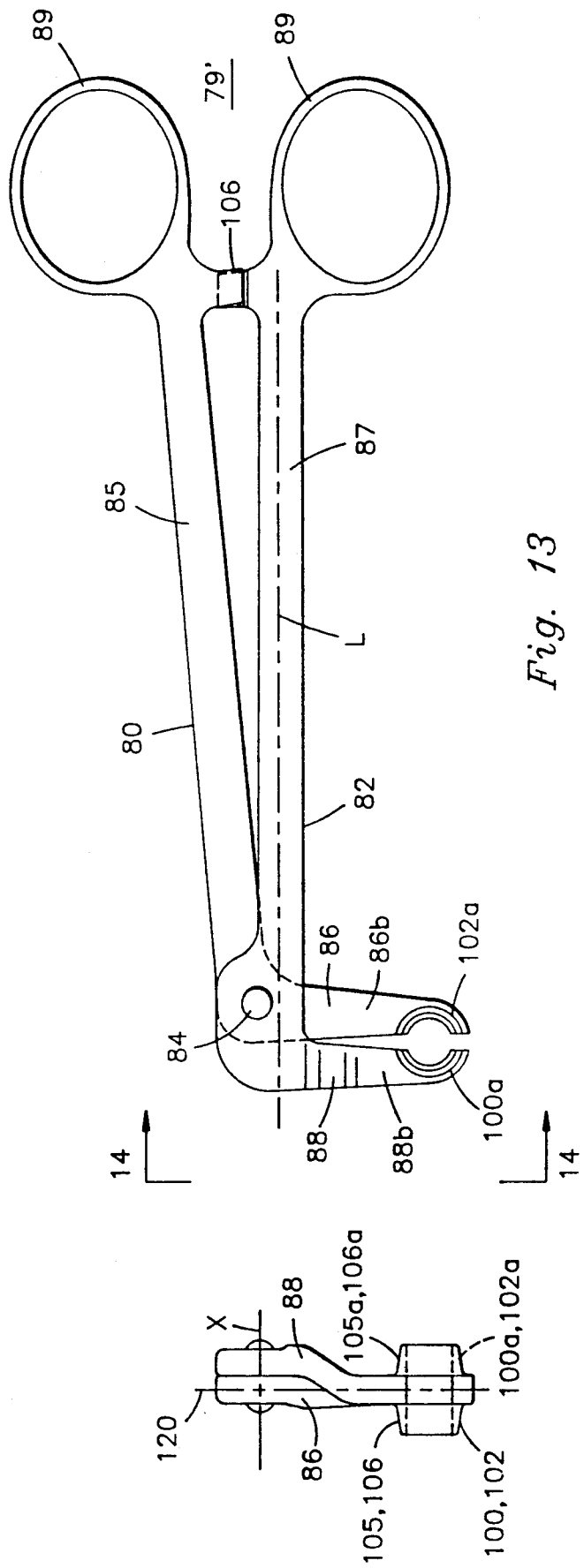
FIG. 13 is a plan view of a modified dental clamp embodying another form of our invention.
FIG. 14 is an end view of the clamp of FIG. 13 taken in the direction of line 14—14 of FIG. 13.

In FIGS. 3 and 14, we show a modified embodiment of our clamp and use the same reference numerals as used in FIGS. 7, 8 and 10-12 for designating corresponding components. In this modified embodiment, the clamp is basically the same as illustrated in FIGS. 7, 8 and 10-12 except that each of the arms (80 and 82) of the clamp is bent in a different manner from the clamp of FIGS. 7, 8 and 10-12. More specifically, in the embodiment of FIGS. 13 and 14 each of arms 80,82 has its distal end located in a reference plane (120) normal to the axis x of the pivot 84, whereas the embodiment of FIGS. 7, 8 and 10-12 the distal end is disposed at an acute angle to the corresponding reference plane (120) that is normal to the axis of the pivot (84) of this clamp. In the embodiment of FIGS. 13 and 14, the distal portion of each jaw (e.g., the portion 88b of jaw 88) extends transversely of the longitudinal axis L of its associated handle (e.g., handle 87).

The embodiment of FIGS. 13 and 14 includes projecting flanges 100 and 102 corresponding to identically designated flanges in the first embodiment and usable for gripping an abutment 40 in substantially the same manner and for the same purpose as explained in connection with the first embodiment.

The particular configuration of the arms 80 and 82 of FIGS. 13 and 14 will sometimes enable the surgeon to obtain more effective access to abutments located near the back of the mouth. For example, the handles, 85 and 87 and the pivot 84 can be located at the side of the patient's face and the transversely-extending jaws 86 and 88 can project into the mouth at the corner of the mouth opening.

By using another set of flanges 100a and 102a on the other sides of the two jaws 86a and b (as shown in FIGS. 13 and 14) one forms a second (but inversely oriented) truncated clamping cone 105a and 106a. The cones 105, 106 and 105a, 106a project at right angles to the reference plane 120 of the handle arms 85, 87 and the jaws 86, 88. With two such clamping cones, a single clamp 79 can be used to service abutments in each of the four quadrants of the mouth. They are the left and right sides of the mouth at each of the upper and lower jaws. Either the flanges 100, 102 are in place to engage a particular abutment in one quadrant (of say the lower jaw on the left side) or the flanges 100a, 102a are so effective for the opposing quadrant (the upper jaw on the left side). Similarly, an abutment in either of the two right-side quadrants can be clamped by the same instrument, but by the opposite pair of flanges.

Thus, the clamp 79 of FIGS. 13 and 14 with two pairs of clamping flanges is effective for use over all four quadrants. With but a single set of flanges, the clamp 79 is alternatively effective in two quadrants.

While we have shown and described a particular embodiment of our invention, it will be obvious to those skilled in the art that various changes and modifications may be made without departing from our invention in its broader aspects; and we, therefore, intend in the appended claims to cover all such changes and modifications as fall within the true spirit and scope of our invention.

What we claim as new and desire to secure by Letters Patents of the United States is:

1. A dental clamp for use in gripping without injury to the gum an abutment that is: (i) mounted on an endosseous-type fixture that is implanted into the host jawbone of a patient, (ii) blocked from rotation with respect to said fixture, and (iii) located with its superior end substantially flush with or beneath the exposed surface of gum tissue closely surrounding the abutment, the clamp comprising:

(a) a pair of arms crossing each other in scissors fashion, (b) a pivot pivotally joining said arms to that portions of said arms on one side of said pivot constitute lockable handles and the portions on the other side of said pivot constitute working portions having free ends and having confronting faces near said free ends that are movable together in response to the handles being moved together and retained in non-rotatable condition when the handles are locked, (c) aligned recesses in said confronting faces that together define an opening extending through said working portions when said confronting faces are in close proximity, which opening when the confronting faces are gripping said abutment is adapted to receive a member that is adapted to be attached to said fixture, and (d) flanges on said working portions projecting laterally therefrom in a location such that the space between said flanges is substantially aligned with said opening when said confronting faces are in close proximity, each of said flanges being dimensioned and shaped so as to be insertable between said abutment and the gum tissue that closely surrounds said abutment, said flanges having rigid and smooth abutment gripping surfaces each of said flanges having a generally semi-cylindrical inner surface bordering said space and an outer surface generally in the shape of a section of a truncated cone having a base adjacent said working portions.

2. The clamp of claim 1 in which said truncated cone has a free end of rounded configuration.

3. The clamp of claim 1 in which each of said flanges tapers in thickness toward the free end of said truncated cone and terminates in a very thin free end which is readily insertable between said abutment and the surrounding gum tissue.

4. The clamp of claim 3 in which said free end of each flange is rounded as viewed in radial planes that include the longitudinal axis of said truncated cone.

5. A dental clamp for use in gripping an abutment that is: (i) mounted on an endosseous-type fixture that is implanted into the jawbone of a patient, (ii) blocked from rotation with respect to said fixture, and (iii) located with its superior end substantially flush with or beneath the exposed surface of gum tissue closely surrounding the abutment, the clamp comprising:

(a) a pair of arms crossing each other in scissors fashion;

(b) a pivot pivotally joining said arms so that the portions of said arms on one side of said pivot constitute handles and the portions on the other side of said pivot constitute working portions having free ends and having confronting faces near said free ends that are movable together in response to the handles being moved together.

(c) and flanges on said working portions projecting laterally therefrom and defining between the flanges a space of generally cylindrical form when the confronting faces of said working portions are in close proximity, each of said flanges being shaped and dimensioned so as to be insertable between said abutment and the gum tissue that closely surrounds said abutment, and said flanges including means adapted to grip said abutment therebetween in response to said handles being urged together when said flanges have been inserted between said abutment and the surrounding gum tissue each of said flanges having a generally semi-cylindrical inner surface bordering said space and an outer surface generally in the shape of a section of a truncated cone having a base adjacent said working portions.

6. The clamp of claim 5 in which said truncated cone has a free end of rounded configuration.

7. The clamp of claim 5 in which each of said flanges tapers in thickness toward the free end of said truncated cone and terminates in a very thin free end which is readily insertable between said abutment and the surrounding gum tissue.

8. The clamp of claim 7 in which said free end of each flange is rounded as viewed in radial planes that include the longitudinal axis of said truncated cone.

9. A dental clamp for use in gripping an abutment that is: (i) mounted on an endosseous-type fixture that is implanted into the jawbone of a patient, (ii) blocked from rotation with respect to said fixture, and (iii) located with its superior end substantially flush with or beneath the exposed surface of gum tissue closely surrounding the abutment, the clamp comprising:

(a) a pair of arms crossing each other in scissors fashion, (b) a pivot pivotally joining said arms so that the portions of said arms on one side of said pivot constitute handles and the portions on the other side of said pivot constitute working portions having free ends and having confronting faces near said free ends that are movable together in response to the handles being moved together.

(c) and flanges on said working portions projecting laterally therefrom and defining between the flanges a space of generally cylindrical form when the confronting faces of said working portions are in close proximity, each of said flanges being shaped and dimensioned so as to be insertable between said abutment and the gum tissue that closely surrounds said abutment, and said flanges being adapted to grip said abutment therebetween in response to said handles being urged together when said flanges have been inserted between said abutment and the surrounding gum tissue, said working portions extending at substantially a right angle transverse to the handle portions, and being in substantially the same plane as said handle portions, one set of two of said flanges projecting at right angles from one of the sides of said working portions, and another set of two of said flanges projecting at right angles from the opposite one of the sides of said working portions, so that said two flanges of the one set project oppositely from said other sets's two flanges, and the two sets of flanges are alternatively engageable with abutments in the upper and lower jawbones of a patient.

10. The clamp of claim 9 in which said two flanges of each of the two sets taper in opposite directions to a thinness insertable between said abutment and surrounding gum tissue.

* * * * *

UNITED STATES PATENT AND TRADEMARK OFFICE
CERTIFICATE OF CORRECTION

PATENT NO. : 5,120,221
DATED : June 9, 1992
INVENTOR(S) : Orenstein et al.

It is certified that error appears in the above-identified patent and that said Letters Patent is hereby corrected as shown below:

On the title page, item (30), References Cited should read:

--FOREIGN PATENT DOCUMENTS
527633    10/1940    Great Britain
1063410   12/1983    Soviet Union--

At column 5, line 16, delete "cross section" and insert therefor --cross-section--; line 48, delete "mixture" and insert therefor --fixture--.

At column 6, line 17, delete "had" and insert therefor --hard--; line 38, delete "10e" and insert therefor --103--; line 62, delete "thc" and insert therefor --the--.

At column 7, line 15, delete "3" and insert therefor --13--.

UNITED STATES PATENT AND TRADEMARK OFFICE
CERTIFICATE OF CORRECTION

PATENT NO. : 5,120,221

DATED : June 9, 1992

INVENTOR(S) : Orenstein et al.

It is certified that error appears in the above-identified patent and that said Letters Patent is hereby corrected as shown below:

In claim 5, column 9, line 7, delete "." and insert therefor --,--.

In claim 9, column 10, line 11, delete "." and insert therefor --,--.

Signed and Sealed this

Seventeenth Day of August, 1993

Attest:

BRUCE LEHMAN

Attesting Officer

Commissioner of Patents and Trademarks